United States Patent [19]
Yamasaki et al.

[11] Patent Number: 5,994,142
[45] Date of Patent: *Nov. 30, 1999

[54] METHOD FOR COLLECTING A METALLIC CONTAMINANTS FROM A WAFER

[75] Inventors: Shinya Yamasaki; Hidemitsu Aoki, both of Tokyo, Japan

[73] Assignee: NEC Corporation, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/915,273

[22] Filed: Aug. 20, 1997

[30] Foreign Application Priority Data

Aug. 23, 1996 [JP] Japan .................................. 8-222343

[51] Int. Cl.$^6$ .................................................. G01N 33/00
[52] U.S. Cl. .............................. 436/73; 436/80; 436/81; 436/83; 436/84; 436/174; 436/175; 422/99; 422/102; 422/104; 206/710; 211/41.18; 134/2
[58] Field of Search .................... 422/99, 102, 104; 436/73, 80, 81, 83, 84, 172, 174, 175, 177, 178; 435/288.3, 305.1; 378/44, 70, 79, 80; 156/626.1; 134/1.3, 2; 206/710, 711; 211/41.17, 41.18

[56] References Cited

U.S. PATENT DOCUMENTS

| | | | |
|---|---|---|---|
| 3,220,300 | 11/1965 | Von Huene | 422/104 X |
| 3,552,548 | 1/1971 | Wallestad et al. | 206/710 |
| 3,719,273 | 3/1973 | Abe . | |
| 4,767,005 | 8/1988 | Onuma et al. | 206/710 |
| 4,886,162 | 12/1989 | Ambrogio | 206/710 |
| 4,990,459 | 2/1991 | Maeda et al. | 436/178 |
| 5,147,607 | 9/1992 | Mochida | 422/102 X |
| 5,162,233 | 11/1992 | Komori et al. | 436/175 X |
| 5,211,717 | 5/1993 | Skoura | 206/710 |
| 5,242,501 | 9/1993 | McDiarmid . | |
| 5,284,802 | 2/1994 | Muraoka et al. | 206/710 X |
| 5,608,155 | 3/1997 | Ye et al. | 73/28.01 |
| 5,633,172 | 5/1997 | Shimazaki et al. | 436/177 |

FOREIGN PATENT DOCUMENTS 4-113611  4/1992  Japan .

OTHER PUBLICATIONS

Realize Inc.; "Atomic Absorption Method"; Feb. 1995; pp. 96–97; publisher unknown.

*Primary Examiner*—Arlen Soderquist
*Attorney, Agent, or Firm*—Hayes, Soloway, Hennessey, Grossman, Hage , P.C.

[57] ABSTRACT

A sampling method for collecting metallic contaminants from a surface of a wafer having an oxide film thereon. A sampling vessel comprises a bottom having a concave inner surface and a convex outer surface, a cylindrical wall extending from the edge of the bottom, and a step section having a plane intercepting an arc plane of the cylindrical wall for adapting the orientation flat of the wafer. Sampling liquid containing 0.1 to 10% HF and hydrogen peroxide dissolves the oxide film and collects the metallic contaminants by swinging the sampling vessel on the convex outer surface of the bottom.

8 Claims, 4 Drawing Sheets

FIG. 1A
PRIOR ART
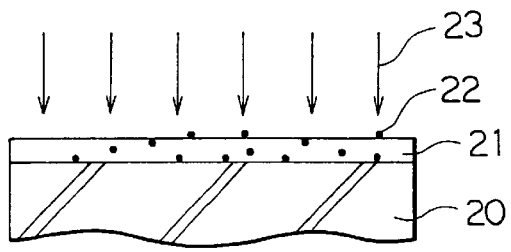
FIG. 1B
PRIOR ART
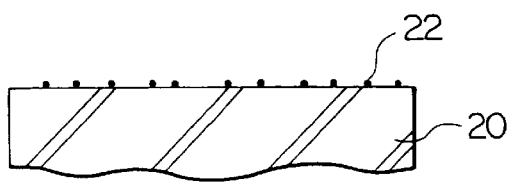
FIG. 1C
PRIOR ART
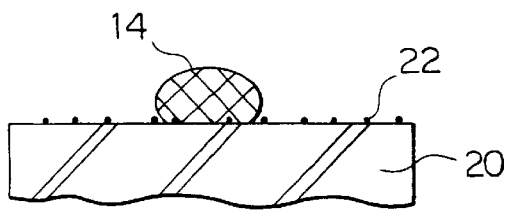
FIG. 2A FIG. 2B FIG. 2C
PRIOR ART  PRIOR ART  PRIOR ART
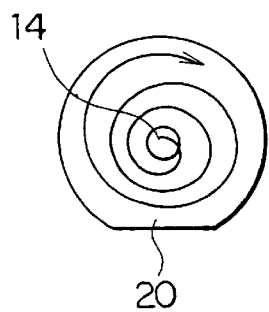 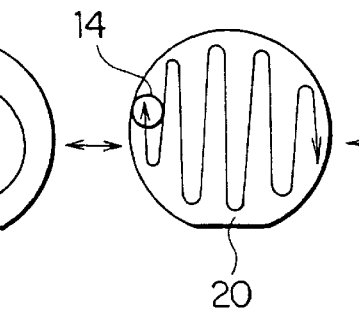 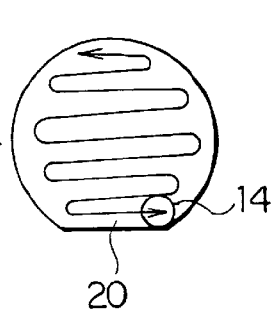

METHOD FOR COLLECTING A METALLIC CONTAMINANTS FROM A WAFER

BACKGROUND OF THE INVENTION (a) Field of the Invention

The present invention relates to a method for collecting metallic contaminants from a wafer and, more particularly to a technique for collecting metallic contaminants from a semiconductor wafer by using a new and improved sampling vessel.

(b) Description of the Related Art

An atomic absorption method (AAS) or an inductive coupling plasma mass spectrometry (ICP-MS) is used as a method for analyzing the amount of metallic contaminants on the surface of a semiconductor wafer. The sample solution used for these analyses is prepared by the steps shown in FIGS. 1A to 1C.

An oxide film 21 formed on the surface of a semiconductor wafer 20 is dissolved by spray of hydrofluoric acid (HF) steam 23 onto the surface of the oxide film 21, an shown in FIG. 1A, to thereby remove the oxide film 21 and expose a silicon surface of the wafer 20, as shown in FIG. 1B. Subsequently, a droplet 14 of a collecting liquid for collecting metallic contaminant is dropped onto the exposed silicon surface of the wafer 20, as shown in FIG. 1C, followed by scanning of the silicon surface by the collecting droplet 14 to collect metallic contaminants 22 into the droplet 14. For instance, the metallic contaminants 22 on the wafer 20 are collected by a spiral scanning (FIG. 2A), or reciprocal scanning (FIG. 2B or FIG. 2C) of the droplet 14. The collecting droplet 14 is recovered by a pipette etc. together with the metallic contaminants 22 as a sample solution, transferred to a dish or vessel for the analysis, and analyzed for the amount of metallic contaminants by the atomic absorption method (AAS) or inductive coupling plasma mass spectrometry (ICP-MS).

During the step of dissolving the oxide film 21 on the silicon surface by HF steam 23, HF droplets may be formed on the silicon surface if the oxide film 21 to be removed is thick to thereby require a large length of time for spray of the HF steam 23 The HF droplets thus formed may move from the main surface of the wafer 20 toward the back surface thereof if the number of HF droplets thus formed is large. In this case, the HF droplets cannot be entirely recovered into the collecting droplet 14, which results in an error in the measurement of the metallic contaminants. A similar situation may occur when the scanning by the collecting droplet 14 is effected at the side surface or back surface of the wafer.

Moreover, the HF droplets formed on the surface of the wafer 20 from the HF steam 23 dilute the collecting droplet 14 to lower the concentration of the metallic contaminants in the collecting droplet 14, thereby lowering the accuracy of the measurement therefrom,

SUMMARY OF THE INVENTION

It is an object of the present invention to provide an improved method for collecting metallic contaminants from a semiconductor wafer, which is capable of improving the accuracy of the measurement of the amount of the metallic contaminants and simplifying the steps for collecting the metallic contaminants.

It is another object of the present invention to provide a collecting vessel for use in the method as mentioned above.

The present invention provides a sampling vessel comprising a bottom section having a concave inner bottom surface and a convex outer bottom surface, a cylindrical wall section having an inner cylindrical surface extending from an edge of the inner bottom surface, and a step section having a plane intercepting a minor arc plane of the inner cylindrical surface and extending parallel to an axis of the inner cylindrical surface from the inner bottom surface.

The present invention also provides a method for collecting a metallic contaminants from a sample surface of a wafer. The method comprises the steps of introducing a sampling liquid into a sampling vessel having a concave inner bottom surface, setting the wafer into the vessel, with the sample surface in contact with the sampling liquid, scanning the sample surface with the sampling liquid to dissolve the metallic contaminants into the sampling liquid, and analyzing the sampling liquid containing the metallic contaminants.

In accordance with the method according to the present invention, metallic contaminants can be collected from the sample surface of the wafer with simple steps and without a loss of droplets containing the metallic contaminants, to obtain a sample solution, which is not diluted by other solution to have a high concentration of the metallic contaminants. Accordingly, an accurate measurement can be effected by using the sample solution prepared by the method.

The above and other objects, features and advantages of the present invention will be more apparent from the following description, referring to the accompanying drawings.

BRIEF DESCRIPTION OF THE DRAWINGS

FIGS. 1A to 1C are sectional views of a wafer during the steps of a conventional method for collecting metallic contaminants from the wafer for preparation of a sample solution;

FIGS. 2A to 2C are top plan views of the wafer for showing scanning by a collecting droplet used in the steps of FIG. 1C;

PREFERRED EMBODIMENTS OF THE INVENTION

Figure 3:
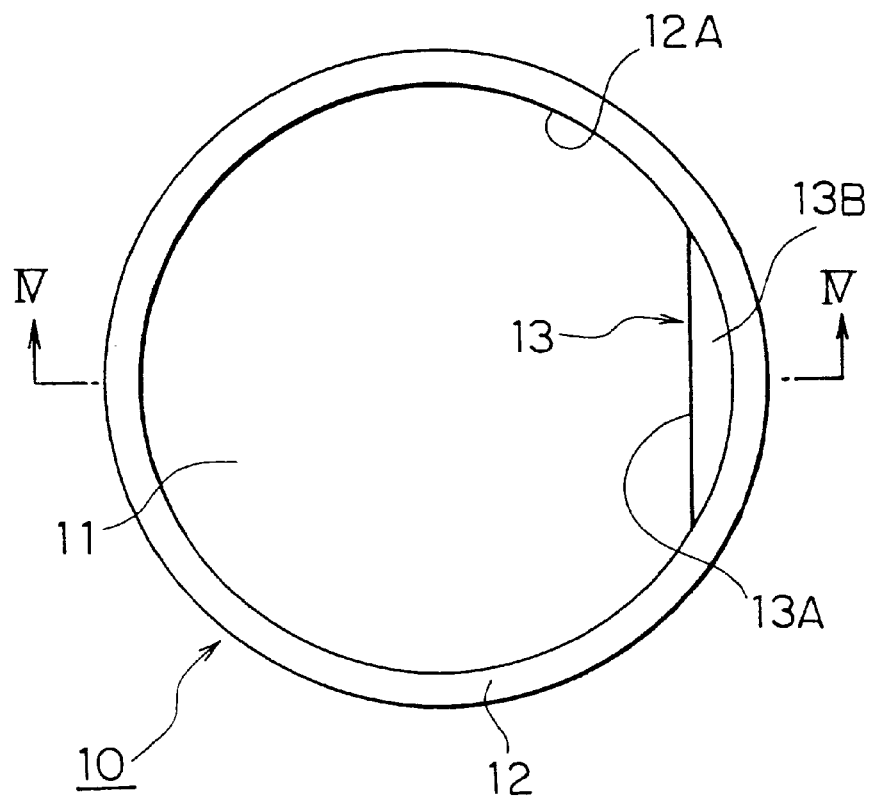
FIG. 3 is a top plan view of a collecting vessel according to an embodiment of the present invention.
Figure 4:
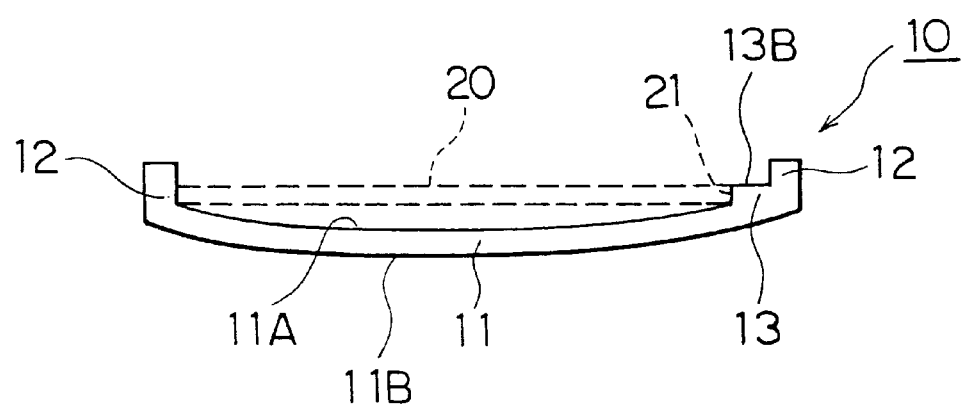
FIG. 4 is a cross-sectional view taken along line IV—IV in FIG. 3.

Referring to FIGS. 3 and 4, a collecting vessel according to an embodiment of the present invention generally designated at numeral 10 is made of a polytetrafluoroethylene (Teflon) implemented as a dish or dish Schale. The collecting vessel 10 comprises a disk-shaped bottom section 11 having a substantially uniform thickness to define a concave inner bottom surface 11A and a convex outer bottom surface 11B, a cylindrical wall section 12 of a relatively small height having an inner cylindrical surface 12A extending from the edge of the inner bottom surface 11A, and a step section 13 having a side surface 13A intercepting a minor arc plane of the inner cylindrical surface 12A of the cylindrical wall section 12 to conform to the orientation flat of a wafer and a top surface 13B lower than the top of the cylindrical wall section 12.

As shown in FIG. 4, the wafer 20 illustrated by a dotted line is received-within the cylindrical wall section 12 of the sampling vessel 10 by setting the wafer 20, with the orientation flat 21 of the wafer 20 in direct contact with the side surface 13A of the step section 13. The inner diameter of the cylindrical wall section 12 is adapted to the diameter of the wafer 20. The concave inner bottom surface 11A of the bottom section 11 is suited to receive a sample solution therein, whereas the convex outer bottom surface 11B of the bottom section 11 is suited to a swinging motion or oscillating motion like a cradle while receiving therein a wafer.

The volume defined between the surface of the wafer 20 and the inner bottom surface 11A of the bottom section 11 ranges preferably between about 0.1 and 1.0 milliliter (ml) for receiving a sample solution.

Figure 5A:
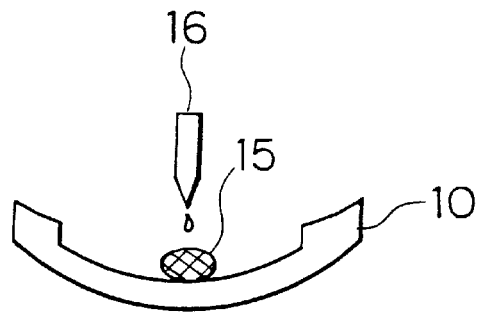
FIGS. 5A to 5F are cross-sectional view of the collecting vessel, showing consecutive steps of a method for collecting metallic contaminants from a wafer to prepare a sample solution according to an embodiment of the present invention.

Referring to FIGS. 5A to 5F, there are shown consecutive steps of a method for collecting metallic contaminants from a wafer according to an embodiment of the present invention. First, as shown in FIG. 5A, a collecting droplet 15 is dropped from a pipette 16 onto the central portion of the sampling vessel 10 in an amount of 0.1 to 1.0 ml. The collecting droplet 15 contains about 0.5 to 10% HF and about 1.0 to 20% hydrogen peroxide, for example. The collecting droplet 15 may be a solution of HF and $H_2O$ instead.

The ingredients of the collecting droplet 15 depends on the metallic contaminants to be collected and include acid such as HF, HCl or $H_2O_2$ or oxidant and water. In this embodiment, the collecting droplet 15 may contain 0.1 to 10% HCl instead of 0.1 to 10% HF for removing the oxide film as well as for collecting the metallic contaminants. It is not practical to use the collecting droplet 15 containing below 0.1% HF or below 0.1% HCl for removing an oxide film having a thickness of 1 $\mu$m or more, because it takes a long time for the removal. A collecting droplet 15 containing more than 10% HF or more than 10% HCl may corrode the analyzer for the sample solution and is not practical.

Figure 5B:
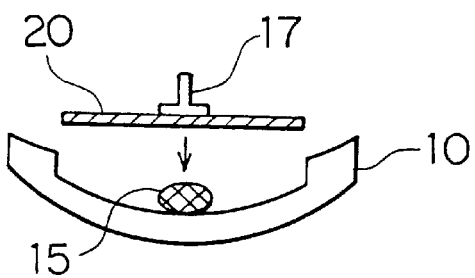
Figure 5C:
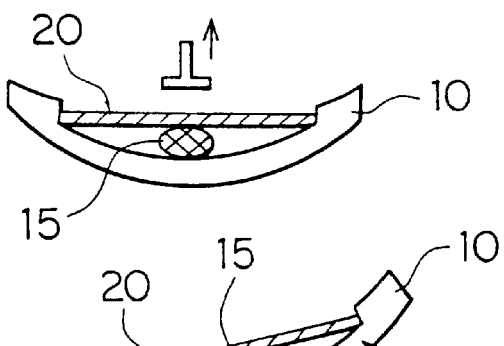

Subsequently,, a sample wafer 20 is carried by a suction element 17 or vacuum conveyer, with the surface of the wafer 20 to be measured being the bottom thereof, as shown in FIG. 5B. The vacuum conveyer 17 conveys the wafer 20, places the wafer 20 within the cylindrical wall section 11 and step section 13, and leaves the wafer 20 in the sampling vessel 10, as shown in FIG. 5C.

If the oxide film to be removed has a large thickness, the sampling vessel 10 may be heated up to a temperature of about 60° C. together with the wafer 20.

Figure 5D:
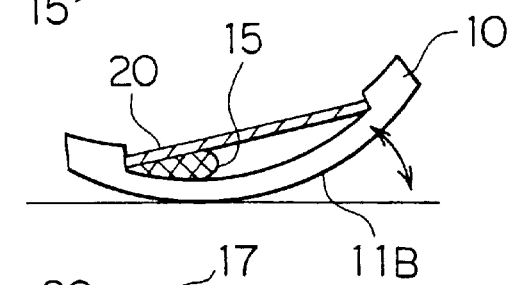

Subsequently, the sampling vessel 10 together with the wafer 20 is iteratively swung in every direction, with the center of the outer bottom surface 113 as the swinging center, to scan the entire surface of the wafer 20 by the collecting droplet 15, thereby dissolving the oxide film formed on the wafer 20 and also collecting the metallic contaminants into the collecting droplet 15. The convex outer bottom surface 11B of the sampling vessel 10 is especially suited to this step, as shown in FIG. 5D. In this embodiment, the collecting droplet 15 is not diluted by other solution or droplets.

Figure 5E:
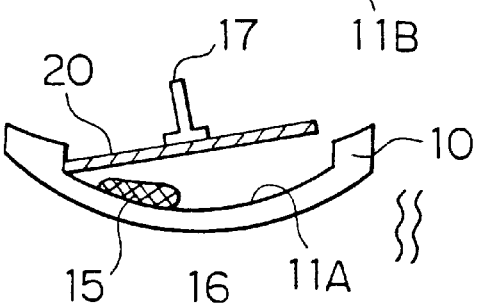

After the swinging step, the wafer 20 in lifted by the vacuum conveyer 17 at the back surface of the wafer and removed from the vessel 10. In this step, the surface of the wafer 20 is first slightly inclined by the vacuum conveyer 17, as shown in FIG. 5E, then the vessel 10 is oscillated, with an edge portion of the wafer 20 being still in contact with the sampling vessel 10. By the oscillation, the droplets then attached to the wafer surface are dropped into the bottom of the vessel 10 to form a part of the sample solution 15 including collecting droplet 15 and metallic contaminants.

Figure 5F:
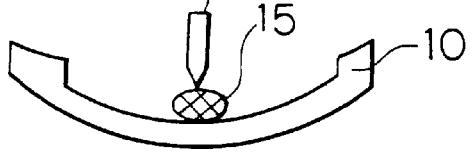

After completion of the removal of the wafer 20 from the sampling vessel 10, the vessel 10 receives at the central part of the bottom section a resultant sample droplet 15, which is recovered by the pipette 16 for analyzing, as shown in FIG. 5F. The metallic contaminants to be analyzed by the embodiment include Fe, Na, Cu, Cr, Ni etc.

The sampling vessel 10 is then subjected to washing by using a mixture of HF and $HNO_3$. A plurality of sampling vessels 10 are preferably prepared for an efficient sampling operation to quickly replace the contaminated vessel by a washed vessel.

In the above embodiment, the removal of the oxide film and collecting the metallic contaminants are effected by a single droplet, which reduces steps for preparation of the sample solution having a high concentration of metallic contaminants.

Figure 6:
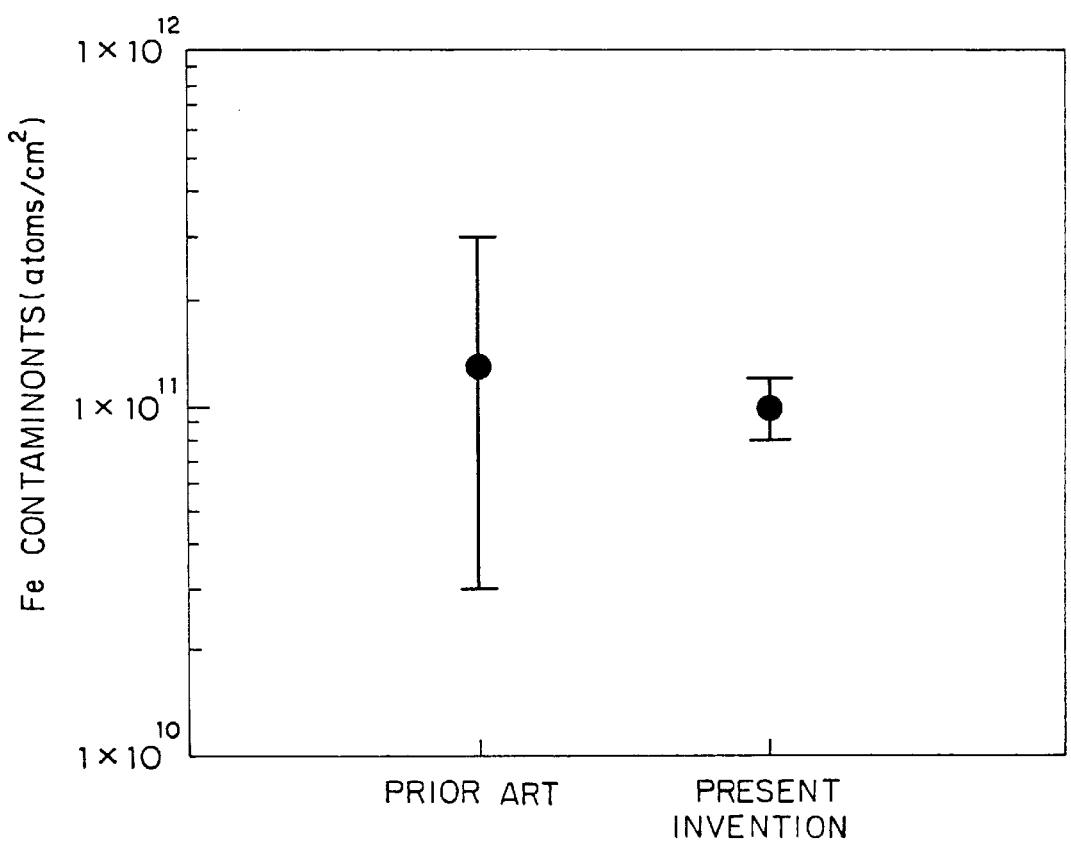
FIG. 6 graphically shows the amounts of metallic contaminants collected by the prior art method and by the present invention.

Referring to FIG. 6 showing the amount of Fe contaminants (atoms/$cm^2$) collected from a wafer by the prior art method and the present invention, the amount of Fe contaminants collected by the sampling vessel according to the present invention less varies during the sampling operation to thereby show an improvement in the accuracy for the measurement.

Since the above embodiments are described only for examples, the present invention is not limited to the above embodiments and various modifications or alterations can be easily made therefrom by those skilled in the art without departing from the scope of the present invention.

What is claimed is:

1. A sampling vessel for receiving a semiconductor wafer of the type having a generally circular peripheral edge with an orientation flat, said vessel consisting of a one piece disk shaped member having a concave inner bottom surface and a convex outer bottom rocking support surface, a cylindrical wall section having an inner cylindrical surface extending from an edge of said inner bottom surface, and a step section having a side surface intersecting a minor arc surface of said inner cylindrical surface and extending parallel to an axis of said inner cylindrical surface from said inner bottom surface, wherein the inner cylindrical surface and the step section side surface conform to the wafer peripheral edge, and the convex outer bottom surface serves as a rocking surface.

2. A sampling vessel as defined in claim 1 wherein said sampling vessel is made of an acid-resistive substance.

3. A sampling vessel as defined in claim 2 wherein said acid-resistive substance is polytetrafluoroethylene.

4. A method for collecting metallic contaminants from a sample surface of a semiconductor wafer of the type having a generally circular peripheral edge with an orientation flat, said method comprising the steps of providing a sampling vessel having a concave inner bottom surface and a convex outer bottom surface, a cylindrical wall section having an inner cylindrical surface extending from an edge of said inner bottom surface, and a step section having a side surface intersecting a minor arc surface of said inner cylindrical surface and extending parallel to an axis of said inner cylindrical surface from said inner bottom surface, wherein the inner cylindrical surface and the step section side surface conform to the wafer peripheral edge, introducing a sampling liquid into said sample vessel, placing the wafer in said vessel, with the orientation flat in contact with the step section side surface and with said sample surface in contact with said sampling liquid, rocking said sampling vessel on its convex outer bottom surface whereby to scan said sample surface with said sampling liquid to dissolve the metallic contaminants into said sampling liquid, and analyzing said sampling liquid containing said metallic contaminants.

5. A method as defined in claim 4 wherein said sampling liquid is selected from the group consisting of a solution containing HF, a solution containing HF and hydrogen peroxide, and a solution containing hydrocliloric acid and hydrogen peroxide.

6. A method as defined in claim 4 wherein said sampling liquid contains 0.1 to 10% HF.

7. A method as defined in claim 4 wherein sampling liquid contains 0.1 to 10% hydrochloric acid and hydrogen peroxide.

8. A method as defined in claim 4 wherein said scanning step includes oscillating said sampling vessel.

* * * * *

UNITED STATES PATENT AND TRADEMARK OFFICE
CERTIFICATE OF CORRECTION

PATENT NO. : 5,994,142
DATED : November 30, 1999
INVENTOR(S) : Yamasaki et al

It is certified that error appears in the above-identified patent and that said Letters Patent is hereby corrected as shown below:

Col. 5, Line 7, "hydrocliloric" should be - -hydrochloric- -.

Signed and Sealed this

Twenty-seventh Day of March, 2001

Attest:

NICHOLAS P. GODICI

*Attesting Officer*  *Acting Director of the United States Patent and Trademark Office*